United States Patent
Soerensen

(10) Patent No.: US 10,080,845 B2
(45) Date of Patent: Sep. 25, 2018

(54) DRUG DELIVERY DEVICE WITH PISTON ROD COUPLING

(71) Applicant: Novo Nordisk A/S, Bagsvaerd (DK)

(72) Inventor: Morten Soerensen, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 109 days.

(21) Appl. No.: 14/892,887

(22) PCT Filed: May 20, 2014

(86) PCT No.: PCT/EP2014/060317
§ 371 (c)(1),
(2) Date: Nov. 20, 2015

(87) PCT Pub. No.: WO2014/187811
PCT Pub. Date: Nov. 27, 2014

(65) Prior Publication Data
US 2016/0095981 A1    Apr. 7, 2016

Related U.S. Application Data

(60) Provisional application No. 61/827,808, filed on May 28, 2013.

(30) Foreign Application Priority Data

May 21, 2013  (EP) ..................... 13168538
May 31, 2013  (EP) ..................... 13170092

(51) Int. Cl.
*A61M 5/315*  (2006.01)
*A61M 5/24*   (2006.01)
*A61M 5/20*   (2006.01)

(52) U.S. Cl.
CPC .......... *A61M 5/31551* (2013.01); *A61M 5/20* (2013.01); *A61M 5/24* (2013.01);
(Continued)

(58) Field of Classification Search
CPC ...... A61M 5/20; A61M 5/24; A61M 5/31525; A61M 5/31543; A61M 5/31553;
(Continued)

(56) References Cited

U.S. PATENT DOCUMENTS 3,144,178 A    8/1964  Sarnoff et al.
3,348,545 A   10/1967  Sarnoff et al.
(Continued)

FOREIGN PATENT DOCUMENTS

CA    2259560 A1   4/1998
EP      37696 A1  10/1981
(Continued)

*Primary Examiner* — Andrew Gilbert
*Assistant Examiner* — Dung Ulsh
(74) *Attorney, Agent, or Firm* — Wesley Nicolas

(57) ABSTRACT

A drug delivery device adapted to receive a cartridge and comprising a housing, an expelling assembly with a threaded piston rod, a threaded nut and a drive element arranged in non-rotational engagement with the piston rod, a drive coupling actuatable between a resetting state in which the piston rod can be moved proximally, and an operational state in which the drive element can drive the piston rod distally, wherein the drive element and the threaded nut are not moved axially relative to the housing when the drive coupling is actuated.

9 Claims, 10 Drawing Sheets

(52) U.S. Cl.
CPC ........ *A61M 5/315* (2013.01); *A61M 5/31525* (2013.01); *A61M 5/31543* (2013.01); *A61M 5/31553* (2013.01); *A61M 5/31563* (2013.01); *A61M 5/31565* (2013.01); *A61M 5/31583* (2013.01); *A61M 5/3155* (2013.01); *A61M 2005/2411* (2013.01)

(58) Field of Classification Search
CPC .......... A61M 5/31565; A61M 5/31583; A61M 5/315; A61M 5/31551; A61M 5/31563; A61M 5/3155; A61M 2005/2411
See application file for complete search history.

(56) References Cited

U.S. PATENT DOCUMENTS

| | | | |
|---|---|---|---|
| 5,593,390 | A | 1/1997 | Castellano et al. |
| 6,090,082 | A | 7/2000 | King et al. |
| 7,175,055 | B2 | 2/2007 | Hansen et al. |
| 7,195,616 | B2 | 3/2007 | Diller et al. |
| 7,427,275 | B2 | 9/2008 | DeRuntz et al. |
| 7,976,494 | B2 | 7/2011 | Kohlbrenner et al. |
| 8,187,233 | B2 | 5/2012 | Harms et al. |
| 8,267,900 | B2 | 9/2012 | Harms et al. |
| 8,298,194 | B2 | 10/2012 | Moller |
| 9,956,349 | B2 | 5/2018 | Soerensen |
| 2008/0119796 | A1 | 5/2008 | Graf et al. |
| 2009/0227955 | A1 | 9/2009 | Hirschel et al. |
| 2009/0254027 | A1 | 10/2009 | Moller |
| 2009/0275914 | A1 | 11/2009 | Harms et al. |
| 2010/0087785 | A1 | 4/2010 | Tschirren et al. |
| 2010/0152671 | A1 | 6/2010 | Raab et al. |
| 2011/0077588 | A1 | 3/2011 | Hirschel et al. |
| 2011/0077595 | A1 | 3/2011 | Eich et al. |
| 2011/0092917 | A1 | 4/2011 | Wei et al. |
| 2011/0152822 | A1 | 6/2011 | Drunk et al. |
| 2012/0035538 | A1 | 2/2012 | Elmen et al. |
| 2012/0083748 | A1 | 4/2012 | Harms et al. |
| 2012/0265151 | A1 | 10/2012 | Nzike et al. |
| 2013/0102972 | A1 | 4/2013 | Jugl et al. |
| 2013/0178802 | A1* | 7/2013 | Nzike .................... A61M 5/24 604/211 |
| 2015/0224266 | A1* | 8/2015 | Plumptre ................ A61M 5/24 604/189 |
| 2016/0045664 | A1* | 2/2016 | Morris .............. A61M 5/31551 604/207 |
| 2016/0067415 | A1* | 3/2016 | Bayer ..................... A61M 5/20 604/211 |
| 2016/0089500 | A1 | 3/2016 | Soerensen |
| 2016/0089501 | A1 | 3/2016 | Soerensen |
| 2016/0114107 | A1 | 4/2016 | Soerensen et al. |

FOREIGN PATENT DOCUMENTS

| | | |
|---|---|---|
| EP | 295075 | 12/1988 |
| EP | 498737 | 8/1992 |
| EP | 554996 | 8/1993 |
| EP | 0937474 A2 | 8/1999 |
| EP | 1064035 A1 | 1/2001 |
| EP | 1996259 A1 | 12/2008 |
| EP | 2274029 A1 | 1/2011 |
| GB | 2477487 A | 8/2011 |
| JP | 2009502273 A | 1/2009 |
| WO | 98/15307 A1 | 4/1998 |
| WO | 2004/020026 A1 | 3/2004 |
| WO | 2006/128794 A2 | 12/2006 |
| WO | 2007017052 A1 | 2/2007 |
| WO | 2007104636 A1 | 9/2007 |
| WO | 2008/037801 A1 | 4/2008 |
| WO | 2008/043188 A1 | 4/2008 |
| WO | 08043188 A1 | 4/2008 |
| WO | 2011/039237 A1 | 4/2011 |
| WO | 2011/040861 A1 | 4/2011 |
| WO | 2011039227 A2 | 4/2011 |
| WO | 2011/051366 A2 | 5/2011 |
| WO | 2011/092326 A1 | 8/2011 |
| WO | 2011/124631 A1 | 10/2011 |
| WO | 2011/154480 A2 | 12/2011 |
| WO | 2011/154481 A1 | 12/2011 |
| WO | 2011/154482 A2 | 12/2011 |
| WO | 2011/154484 A1 | 12/2011 |
| WO | 2011/154489 A1 | 12/2011 |
| WO | 2011/154490 A1 | 12/2011 |
| WO | 11154480 A2 | 12/2011 |
| WO | 2012/017035 A1 | 2/2012 |
| WO | 12020085 A1 | 2/2012 |

\* cited by examiner

DRUG DELIVERY DEVICE WITH PISTON ROD COUPLING

CROSS-REFERENCE TO RELATED APPLICATIONS

This application is a 35 U.S.C. § 371 National Stage application of International Application PCT/EP2014/060317 (published as WO2014/187811), filed May 20, 2014, which claims priority to European Patent Application 13168538.0, filed May 21, 2013, and European Patent Application 13170092.4, filed May 31, 2013; this application claims priority under 35 U.S.C. § 119 to U.S. Provisional Application 61/827,808; filed May 28, 2013.

The present invention generally relates to drug delivery devices adapted to receive a drug filled cartridge and expel a dose therefrom.

BACKGROUND OF THE INVENTION

In the disclosure of the present invention reference is mostly made to the treatment of diabetes, however, this is only an exemplary use of the present invention.

The most common type of injection devices adapted to receive a drug filled cartridge and expel a dose therefrom are generally pen-formed and utilizes a so-called cartridge holder adapted to receive and mount a cartridge in the device. Correspondingly, most pen-formed drug delivery devices comprises a generally cylindrical cartridge holder for receiving and holding a generally cylindrical drug-filled cartridge in a mounted position, the cartridge comprising a proximally facing and axially displaceable piston, and a main body with a housing in which a drug expelling mechanism is arranged, the mechanism comprising an axially displaceable piston rod adapted to engage the piston of a mounted cartridge to thereby expel a dose of drug from the cartridge. Between the cartridge holder and the main body a connection means is provided allowing a user to remove the cartridge holder from the main body and reattach it when a used cartridge has been exchanged with a new cartridge. The cartridge is in most cases inserted in the cartridge holder by axial movement through a proximal opening, see e.g. WO 2011/124631, EP 0 937 474 and WO 2011/092326. The connection means may be in the form of a threaded connection or a bayonet coupling. Depending on the design of the drug delivery device the piston rod has to be moved proximally (i.e. "reset") by rotation when an empty cartridge is exchanged with a full cartridge, or the piston rod can be reset by being pushed axially, e.g. by unlocking the piston rod when the cartridge holder is removed from the main body, this as disclosed in for example US 2009/0275914, WO 2011/051366 and WO 2011/154482. The latter document discloses a drive mechanism with a stop member, a drive member and a rotation member, wherein either the stop member or the rotation member may be axially locked the other two being axially displaceable when operated between the resetting and operational state.

Alternatively, the drug delivery device may comprise an integrated (i.e. for the user non-removable) cartridge holder adapted to axially receive a cartridge through a distal opening. Such a device is often named "front loaded", see e.g. WO 2004/020026 and US 2011/152822. The cartridge holder may be provided with gripping means adapted to hold and release an axially inserted cartridge.

Having regard to the above, it is an object of the present invention to provide a drug delivery device adapted to receive a drug-filled cartridge in a simple and effective way, the arrangement being to a high degree user-friendly, accurate and reliable.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device is provided adapted to receive a cartridge comprising a cylindrical body portion, a distal outlet portion and an axially displaceable piston. The drug delivery device comprises a housing, a cartridge holder adapted to receive and hold a cartridge, and an expelling assembly. The expelling assembly comprises a piston rod comprising an external thread and being adapted to engage and axially displace a piston in a loaded cartridge in a distal direction to thereby expel a dose of drug from the cartridge, a nut portion arranged non-moveable relative to the housing (i.e. non-rotationally and axially non-moveable) and comprising a threaded bore being in rotational engagement with the external thread of the piston rod, and a primary drive element arranged in non-rotational engagement with the piston rod, the piston rod being axially moveable relatively to the primary drive element, whereby rotation of the primary drive element provides that the piston rod is moved axially through the nut portion. The expelling assembly further comprises a drive assembly adapted to rotate the primary drive element, and a drive coupling being actuatable between (i) a resetting state in which the piston rod can be moved proximally, and (ii) an operational state in which the primary drive element can drive the piston rod distally. The drug delivery device further comprises user operated actuation means actuatable from a loading state to an operational state, wherein the drive coupling is actuated from the resetting state to the operational state when the actuation means is actuated from the loading state to the operational state, and wherein the primary drive element is not moved axially when the drive coupling is actuated.

By this arrangement a coupling is provided in which the essential elements for the piston drive, i.e. the nut and the piston rod engaging drive element, are not moved axially, this allowing an axially compact design. Additionally, as the drive element is not adapted to move axially and thus has a well-defined axial position, it can be used as part of a safety system in combination with a further element rotationally mounted on the piston rod, e.g. as disclosed in WO 2007/017053.

The primary drive element may be axially locked directly to the housing, this providing a system with reduced slack. For example, the nut may be formed as part of the housing and the primary drive element may be coupled to the nut portion to allow rotation there between.

The expelling assembly may further comprise a secondary drive element rotationally driven by the drive assembly, the drive coupling comprising a coupling element moveable by the actuation means between a resetting position, corresponding to the resetting state, wherein the primary and secondary drive elements are rotationally de-coupled, and an operational position corresponding to the operational state, wherein the primary and secondary drive elements are rotationally coupled. The primary drive element, the drive coupling and the secondary drive element may be arranged concentrically.

Also the secondary drive element may be axially locked relative to the housing, with the coupling element being axially moveable between the resetting and operational positions.

Depending on the actual design of the drive mechanism, the piston rod may be prevented from being moved proximally in the operational state.

The cartridge holder may be of the "traditional" type adapted to be connected to the housing by a relative motion there between, the cartridge holder or the cartridge serving as the actuation means.

Alternatively, the cartridge holder may be front-loaded and attached to the housing, the cartridge holder having (i) a receiving state in which a cartridge can be inserted and received in a proximal direction, and (ii) a holding state in which an inserted cartridge is held in an operational position. The actuation means for the coupling and the cartridge holder may be the same such that the cartridge holder is actuated from the receiving state to the holding state when the actuation means is actuated from the loading state to the operational state. Alternatively the actuation means for actuating the cartridge holder may be different from the actuation means for actuating the coupling.

In an exemplary embodiment the cartridge holder comprises distally arranged holding means actuatable from (i) a receiving state allowing a cartridge to be inserted into the cartridge holder in a proximal direction, to (ii) a holding state in which a received cartridge is prevented from moving distally, when the cartridge holder is actuated from the receiving state to the holding state. The holding means may comprise one or more flexible locking arms, e.g. two opposed arms, each having a distal gripping portion being moved towards the central axis when the holding means is actuated from the receiving state to the holding state. The cartridge holder may be arranged to be moved proximally relative to the housing when the actuation means is actuated from the loading state to the operational state.

In an exemplary embodiment the actuation means is actuatable from a loading state through an intermediate state to an operational state, wherein (i) the cartridge holder is actuated from the receiving state to the holding state when the actuation means is actuated from the loading state to the intermediate state, and (ii) the coupling is actuated from the resetting state to the operational state when the actuation means is actuated from the intermediate state to the operational state.

The above-described user operated actuation means may comprise an actuation sleeve being rotationally actuatable relative to the housing from the loading state through the intermediate state to the operational state, wherein the actuation sleeve encloses at least a portion of a mounted cartridge, the actuation sleeve comprising inspection means allowing at least a portion of an enclosed cartridge portion to be visually inspected. The actuation sleeve may comprise one or more openings or be at least partially transparent, thereby providing the inspection means. The cartridge holder may be provided with one or more lateral openings or be at least partially transparent, this allowing a loaded cartridge to be inspected visually through both the cartridge holder and the actuation sleeve, this being relevant when the cartridge holder as well as the actuation sleeve encloses substantially the entire length of a loaded cartridge.

When the cartridge is described as being "held" or "locked" in place it is meant that the cartridge is prevented from being moved distally, however, in many cases it will be allowed to rotate just as it may be allowed to be moved proximally, the latter being determined by other structures or the actual design of the expelling mechanism. For example, a spring may provide a distally directed biasing force on an inserted cartridge, such a design allowing the cartridge to be pushed somewhat proximally against the biasing spring force.

In an exemplary embodiment the cartridge holder comprises distally arranged holding means actuatable from (i) a receiving state allowing a cartridge to be inserted into the cartridge holder in a proximal direction, to (ii) a holding state in which a received cartridge is prevented from moving distally, when the cartridge holder is actuated from the receiving state to the holding state. The holding means may comprise one or more flexible locking arms, e.g. two opposed arms, each having a distal gripping portion being moved towards the central axis when the holding means is actuated from the receiving state to the holding state. The cartridge holder may be arranged to be moved proximally relative to the housing when the actuation means is actuated from the loading state to the intermediate state.

In an exemplary embodiment the actuation means comprises an actuation member which relative to the housing can be rotated from a loading position through an intermediate position to an operational position corresponding to the loading state, the intermediate state and the operational state. The cartridge holder may be coupled to move rotationally with the actuation member.

The drive assembly may comprise setting means allowing a user to set a dose amount to be expelled. The drive assembly may further comprise a stop member in threaded engagement with the piston rod, a setting member coupled to the setting means such that rotation of the setting means during dose setting causes the setting member to rotate, wherein the stop member is coupled to the setting member and the piston rod such that relative rotation between the setting member and the piston rod during dose setting causes the stop member to move proximally on the piston rod, and wherein the stop member rotates with piston rod during dose expelling, the stop member abutting a proximally-facing surface of the primary drive element when the set dose has been expelled. The drive assembly may further comprise a drive spring being strained during dose setting corresponding to the set dose, and user actuated release means for releasing the drive spring to thereby move the piston rod in the distal direction corresponding to the set dose.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. When it is defined that members are mounted axially free to each other it generally indicates that they can be moved relative to each other, typically between defined stop positions whereas when it is defined that members are mounted rotationally free to each other it generally indicates that they can be rotated relative to each other either freely or between defined stop positions. The terms "assembly" and "subassembly" do not imply that the described components necessarily can be assembled to provide a unitary or functional assembly or subassembly during a given assembly procedure but is merely used to describe components grouped together as being functionally more closely related.

Figure 1A:
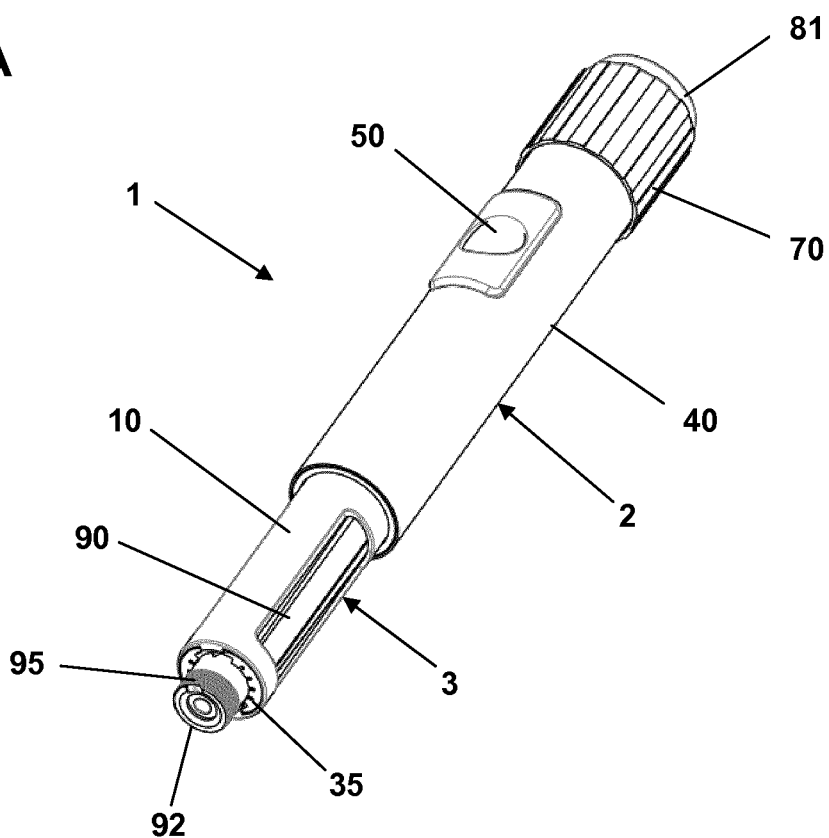
FIGS. 1A and 1B show a front-loaded drug delivery device with respectively without a drug cartridge mounted.
Figure 1B:
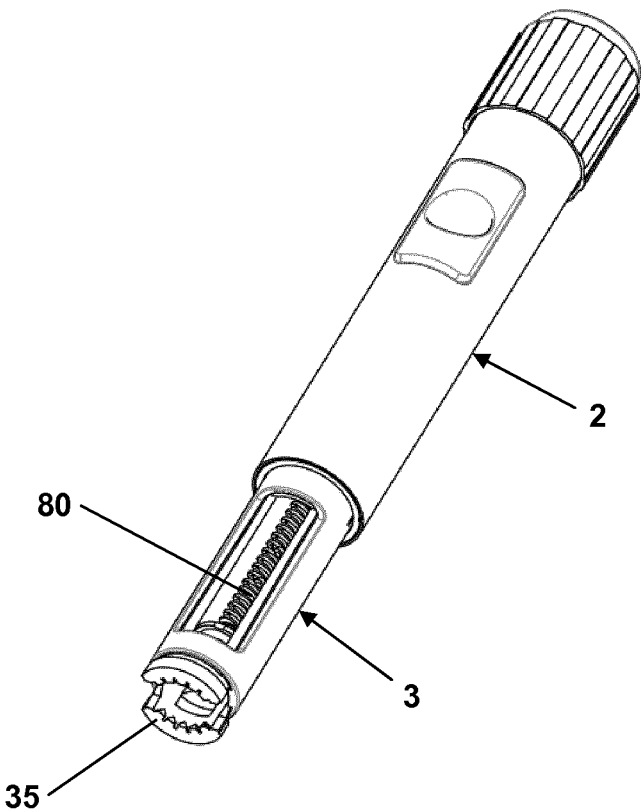

Referring to FIGS. 1A and 1B a pen-formed drug delivery device 1 will be described. More specifically, the pen device comprises a cap part (not shown) and a main part having a proximal body or drive assembly portion 2 with a housing 40 in which a drug expelling mechanism is arranged or integrated, and a distal cartridge holder portion in which a drug-filled transparent cartridge 90 with a distal needle-penetrable septum 92 is arranged and retained in place by a cartridge holder assembly 3 mounted to the proximal portion. The cartridge may for example contain an insulin, a GLP-1 or a growth hormone formulation. The device is designed to be loaded by the user with a new cartridge through a distal receiving opening in the cartridge holder assembly, the cartridge being provided with a piston driven by a piston rod 80 forming part of the expelling mechanism. A proximal-most rotatable dose setting member 70 serves to manually set a desired dose of drug shown in display window 50 and which can then be expelled when the release button 81 is actuated. In the shown drug delivery device the expelling mechanism comprises a spring which is strained during dose setting and then released to drive the piston rod when the release button is actuated. Alternatively the expelling mechanism may be fully manual in which case the dose setting member and the release button moves proximally during dose setting corresponding to the set dose size, and then moved distally by the user to expel the set dose. The cartridge is provided with distal coupling means in the form of a needle hub mount 95 having, in the shown example, an external thread adapted to engage an inner thread of a corresponding hub of a needle assembly. In alternative embodiments the thread may be combined with or replaced by other connection means, e.g. a bayonet coupling. The shown exemplary hub mount further comprises a circumferential flange with a number of distally facing pointed projections serving as a coupling means for the cartridge holder assembly as will be described in more detail below. A hub mount of the shown type is described in U.S. Pat. No. 5,693,027. Alternatively the needle hub mount may be formed as part of the cartridge holder, e.g. in the form of a "split" hub mount having two parts arranged on each of the gripping shoulders, see below.

As shown, the cartridge holder assembly 3 has the same general appearance as a traditional cartridge holder which is detachably coupled to the housing by e.g. a threaded coupling or a bayonet coupling and into which a new cartridge can be received as well as removed through a proximal opening, i.e. it comprises no additional user operated release or locking means. Instead, what appears merely to be the cartridge holder per se is in fact user operated coupling means in the form of an outer rotatable tube member 10 operated by the user to control movement of cartridge holding means in the form of an inner cartridge holder member 30 (see FIG. 2A) to thereby open and close gripping shoulders 35 configured to grip and hold a cartridge. More specifically, the gripping shoulder 35 is provided with a plurality of gripping teeth 38 spaced circumferentially to provide a plurality of gaps, each tooth having a triangular configuration with a proximally oriented pointed end, thereby creating a plurality of gaps having a distally oriented pointed configuration, this allowing the above-described distally facing pointed projections on the cartridge to be received between the teeth 38 to thereby serve as a gripping means when the cartridge holding means has been moved into engagement with the cartridge. In this way an easy-to-use front loaded drug delivery device is provided which appears as a traditional rear loaded device and which is also actuated by rotational movement to mount and remove a cartridge, the resemblance providing for ease of acceptance and adaptation among users accustomed to traditional types of rear loaded drug delivery devices.

When it is time to mount a new cartridge the outer tube member is rotated e.g. 90 degrees by which action the gripping shoulders 35 are moved distally and slightly outwards, this allowing the mounted cartridge to be removed. For ease of operation the cartridge may be moved distally a certain distance as the shoulders are moved, e.g. by engagement with arms forming the gripping shoulders and/or by additional spring means providing a biasing distally directed force. FIG. 1B shows the device with the cartridge removed and the gripping shoulders in their un-locked "open" position in which a cartridge can be removed and a new inserted. Depending on the design of the locking and actuation mechanism the gripping shoulders may be able to be left in the open position or they may be retracted automatically as the outer tube member is rotated backwards by return spring means. Whether or not a spring is provided the cartridge holder may be provided with locking means allowing the outer tube member to be securely parked in either the open or closed position, e.g. by a rotational snap lock. When a new cartridge is inserted the drive expelling means has to be in a state allowing the piston rod to be pushed proximally by the piston of the new cartridge. An exemplary embodiment of a coupling mechanism providing this functionality will be described below.

Figure 2A:
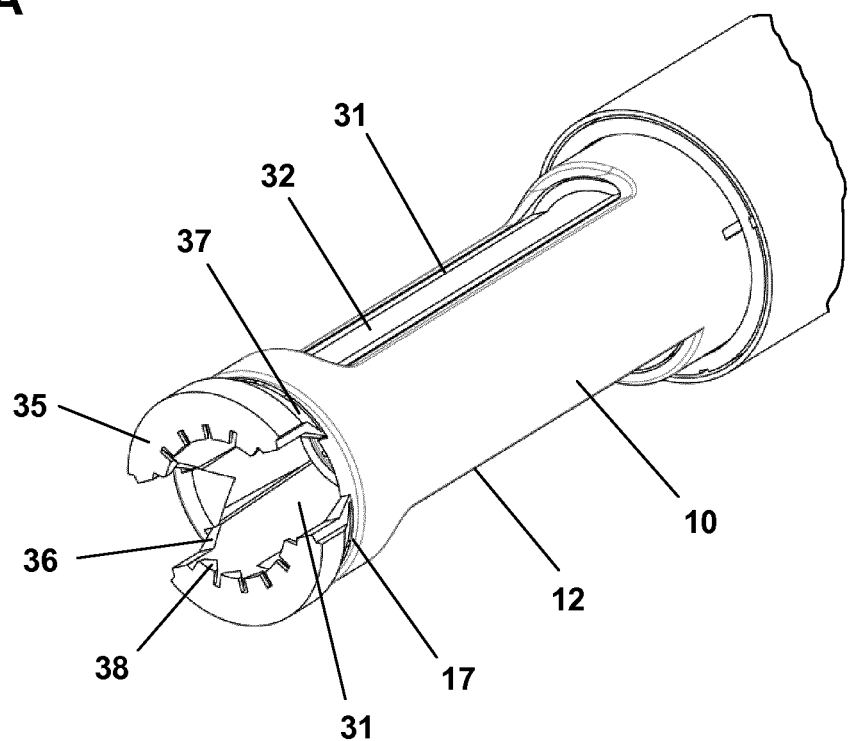
FIGS. 2A and 2B show detail views of the cartridge holder of FIG. 1A in an open respectively closed state.
Figure 2B:
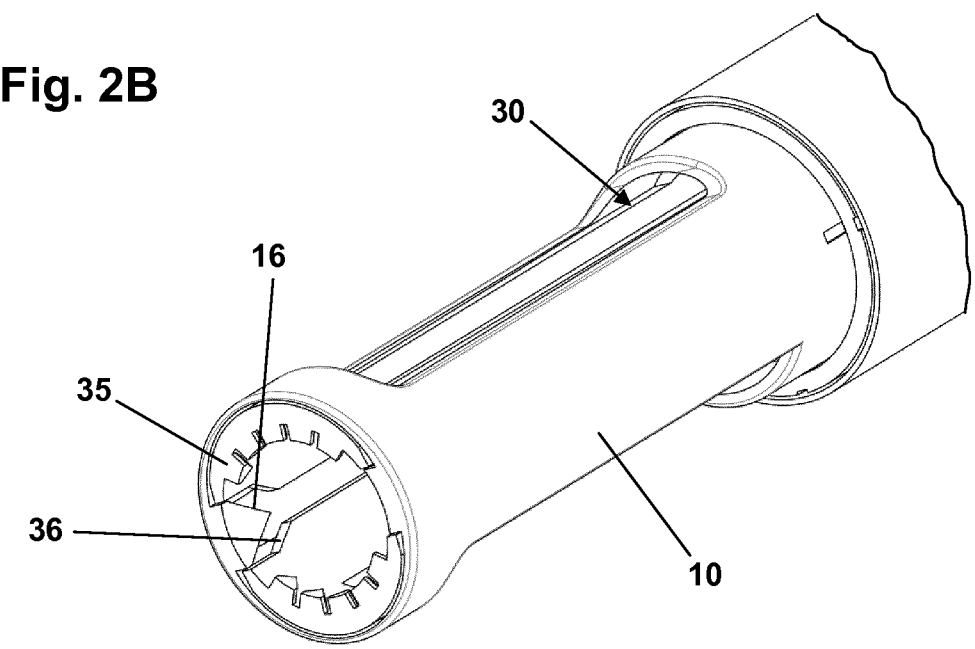

The mechanical arrangement providing the above-described user-interface, i.e. rotation of an outer tubular sleeve member moves gripping shoulders in and out, can be provided in numerous ways. As shown in FIGS. 2A and 2B the cartridge holder 30 comprises two opposed flexible arms 31 extending from a proximal ring portion arranged in axially guided sliding and thus non-rotational engagement with the outer tubular sleeve member, each arm being provided with a gripping shoulder 35. By this arrangement the gripping shoulders will rotate together with the outer tubular sleeve member and thus relative to the housing 40 as they are moved axially. In shown embodiment two opposed windows 32 are formed in the gripping member, one in each arm, each window being aligned with a corresponding window 12 formed in the outer tubular sleeve member, the two pairs of windows moving together in rotational alignment. Alternatively the gripping member and/or the outer tubular sleeve member may be manufactured fully or partly from a transparent material. Each gripping shoulder comprises an outer inclined and curved surface 37 adapted to engage a correspondingly curved distal actuation edge 17 of the outer tubular sleeve member 10, as well as a pair of inclined edge portions 36 adapted to engage a pair of corresponding inclined actuation surfaces 16 arranged on the inner surface of the actuation sleeve. By this arrangement the inclined actuation surfaces 36 will force the gripping shoulders outwardly to their open position as the actuation surfaces 36 are moved distally and into sliding contact with the sleeve actuation surfaces 16. Correspondingly, when the arms are moved proximally the outer curved surfaces 37 engage the actuation edges 17 and are thereby forced inwardly into their gripping position.

In alternative embodiments the gripping members may be arranged non-rotationally relative to the body portion 2, just as the actuation sleeve may be arranged to be moved axially only or by a combination of axial and rotational movement.

Figure 3:
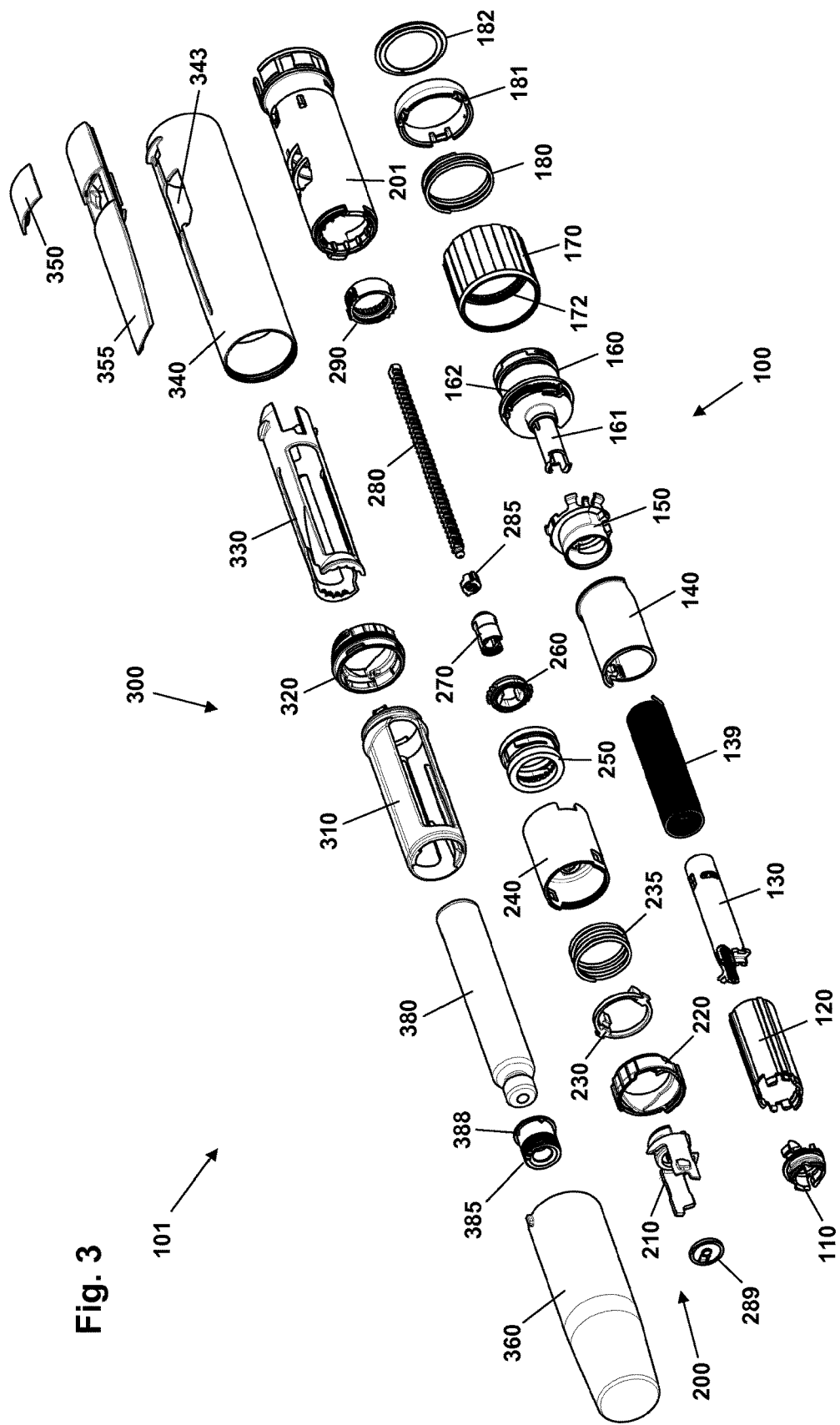
FIG. 3 shows in an exploded view components of a pen device of the type shown in FIG. 1A.
Figure 4:
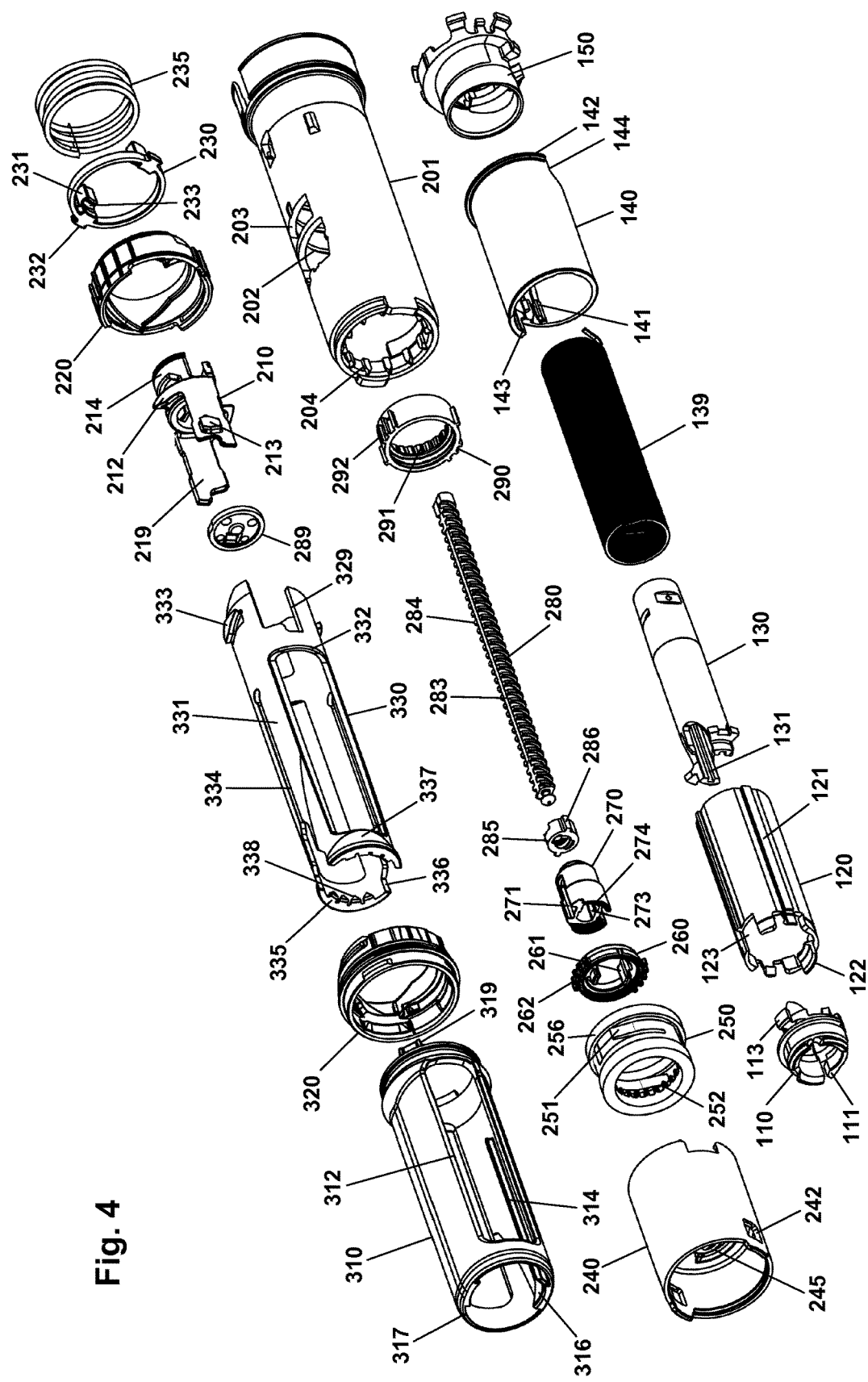
FIG. 4 shows in an exploded view a part of the components shown in FIG. 3.

FIG. 3 shows an exploded view of a pen-formed drug delivery device 101 of the type shown in FIGS. 2A and 2B. As aspects of the invention relate to the working principles of such a pen, an exemplary embodiment of a complete pen mechanism and its features will be described, most of which are merely illustrative examples of features and designs adapted to work with and support the aspects of the present invention. The pen will be described as comprising three assemblies, a dose setting assembly 100, a dose expelling and coupling assembly 200, and a cartridge holder and housing assembly 300. FIG. 4 corresponds to FIG. 3, however, to provide a better detail view some of the components are not shown and the remaining components have been rearranged.

More specifically, the dose setting assembly 100 comprises a ratchet member 110, a ratchet tube 120, a reset tube 130, a helical torque spring 139, a scale drum 140 with an outer helically arranged row of dose numerals (not shown), a spring base member 150, a button module 160, a user-operated dial member 170 for setting a dose of drug to be expelled, and a release button subassembly comprising a button 181, a button top window 182 and a button spring 180. The button module may be in the form a simple mechanical member adapted to be incorporated in the described mechanical design, or it may be in the form of an electronic module adapted to detect relative movement between different members in order to provide an electronic dose logging feature, however, the latter module version is incorporated in the same way as the simple version. The button window is adapted to be used when the button module is in the form of a logging module having a proximally facing display. Otherwise the button ring and top may be manufactured as a single button member. The proximal end of the reset tube member 130 is adapted to be connected rotationally and axially locked to the distal tube portion of the button module 160, however, this arrangement is mainly to allow the button part to be provided as a separate module, e.g. with or without electronic features.

Functionally, in an assembled state, the button module distal tube portion 161 is mounted axially and rotationally locked to the reset tube 130 which is mounted concentrically inside the ratchet tube, the two tubes being axially and rotationally locked at their distal ends, the latter arrangement being mainly for the purpose of moulding and subsequent assembly of the two components. However, the split design would also allow the two members to be connected similar to a universal joint e.g. via two opposed projections on the reset tube received in corresponding openings on the ratchet tube, this providing a mechanism with improved kinematic mobility being less over-constrained.

The ratchet member 110 is mounted axially locked on the reset tube but is allowed to rotate a few degrees (see below) by means of axial snap connection means on the reset tube, this "play" being controlled by the control projection 113 arranged in a ratchet tube cut-out 123. In this way a rotationally flexible connection is provided between the ratchet member and the reset tube, and thereby also between the ratchet member and the ratchet tube.

The reset tube comprises on its inner surface two opposed longitudinal grooves 131 adapted to engage radial projections 286 of the EOC member (see below), whereby the EOC can be rotated by the reset tube but is allowed to move axially. A clutch member 290 with outer spline elements is mounted axially locked on the ratchet member; this providing that the ratchet tube via the ratchet member can be moved axially in and out of rotational engagement with the housing via the clutch member. The dial member 170 is mounted axially locked but rotationally free on the inner housing proximal end. During dose setting the dial member is rotationally locked to the reset tube via toothed engagement with the button module (see below), rotation of the dial member thereby resulting in a corresponding rotation of the reset tube and thereby the ratchet tube and ratchet member. The release button 181 is axially locked to the reset tube via the button module but is free to rotate. The return spring 180 provides a proximally directed force on the button and the thereto mounted reset tube. The scale drum 140 is arranged in the circumferential space between the ratchet tube and the inner housing, the drum being rotationally locked to the ratchet tube via cooperating longitudinal splines 121, 141 and being in rotational threaded engagement with the inner surface of the inner housing via cooperating thread structures 142, 202, whereby the row of numerals passes window openings 203, 343 in the inner respectively outer housing (see below) when the drum is rotated relative to the housing by the ratchet tube. The proximal end of the scale drum comprises a stop surface 144 adapted to engage a corresponding stop surface on the spring base member 150 to thereby provide a rotational stop for an initial (or end) rotational position, and the distal end of the scale drum comprises a further stop surface 143 adapted to engage a corresponding stop surface on the proximal housing inner surface when the maximum dose has been reached during dose setting, e.g. 100 units of insulin (IU). The torque spring 139 is arranged in the circumferential space between the ratchet tube and the reset tube and is at its proximal end secured to the spring base member 150 and thus the housing and at its distal end to the ratchet member 110, whereby the spring is strained when the ratchet member is rotated relative to the housing by rotation of the dial member. A ratchet mechanism with a flexible ratchet arm 111 is provided between the ratchet member and the clutch member, the latter being provided with an inner circumferential teeth structure 291 (or toothing), each tooth providing a ratchet stop such that the ratchet tube is held in the position to which it is rotated by a user via the reset tube when a dose is set. In order to allow a set dose to be reduced a ratchet release mechanism in the form of a release member 122 is provided on the ratchet tube and acting on the ratchet member to move it inwards and thereby out of engagement with the teeth structure, this allowing a set dose to be reduced by one or more ratchet increments by turning the dial member in the opposite second direction, the release mechanism being actuated when the ratchet tube is rotated the above-described few degrees of play relative to the ratchet member. Alternatively the release mechanism could be arranged on the reset tube.

The dose expelling and coupling assembly 200 comprises a fork member (or "slider") 210, a distal housing 220, a ring member 230, a compression spring 235, a nut housing 240 comprising a central portion with a threaded nut bore 245, a drive assembly comprising an outer drive member 250, a coupling member 260 and an inner drive member 270, a threaded piston rod 280 having an external thread 285 and two opposed longitudinal planar surfaces 283, an end-of-content (EOC) member 285, a piston rod washer 289, a clutch member 290 and a proximal housing 201.

Functionally, in an assembled state, the inner drive member 270 comprising a central bore with two opposed planar surfaces is mounted axially locked but rotationally free on the central portion of the nut housing 240 by means of a circumferential flange 244 (see FIG. 8) surrounding the proximal opening of the nut bore and a pair of opposed gripping flanges 274 arranged on the distal end of the inner drive member. The central nut portion is carried in the nut housing by arm structures 246 (see FIG. 8) providing openings through which the proximal-most part 214 of the fork element is arranged. The piston rod is arranged through the two aligned bores with the threaded bore 245 receiving the piston rod thread 285 and with the two opposed planar surfaces 273 of the inner drive member in engagement with the opposed planar surfaces 283 on the piston rod, whereby rotation of the inner drive member results in rotation and thereby distal axial movement of the piston rod due to the threaded engagement between the piston rod and the nut bore. On the piston rod the end-of-content (EOC) member 285 is threadedly mounted and on the distal end the washer 289 is axially mounted but rotationally free. The washer can be considered the part of the piston rod which is adapted to directly engage a cartridge piston. The EOC member comprises a pair of opposed radial projections 286 for engagement with the reset tube (see above).

The ring-formed outer drive member 250, which is mounted axially locked but rotationally free in the nut housing, is in permanent rotational engagement with the ring-formed clutch member 290 by means of cooperating coupling structures, such that the engagement allows axial movement of the clutch member relative to the outer drive member. The outer drive member further comprises a pair of opposed circumferentially extending flexible ratchet arms 251 adapted to uni-directionally engage corresponding ratchet teeth 241 (see FIG. 7A) arranged on the nut housing inner surface. In the embodiment of FIG. 4 the outer drive member is provided with a proximal supporting ring structure 256. The clutch member is provided with outer spline elements 292 adapted to engage corresponding spline elements 204 on the proximal housing inner surface, this allowing the clutch member to be moved between a rotationally locked proximal position, in which the splines are in engagement with the inner housing, and a rotationally free distal position in which the splines are out of engagement with the inner housing.

Between the outer and inner drive members the ring-formed coupling member 260 is arranged, this providing that the drive assembly can be actuated between a resetting state (see below) in which the inner drive member and thereby the piston rod can be rotated relative to the outer drive member and thereby the nut housing, and an operational state in which the inner and outer drive members are rotationally locked to each other. The coupling member is mounted axially locked but rotationally free on the proximal end portion 214 of the fork member 210, as well as rotationally locked but axially free on the inner drive member via cooperating spline structures 261, 271. The coupling member comprises circumferentially arranged outer coupling teeth 262 adapted to be moved axially in and out of engagement with corresponding coupling teeth 252 arranged circumferentially on the inner surface of the outer drive member. By this arrangement the coupling member can be actuated via axial movement of the fork member between a proximal position in which the coupling member and outer drive member are rotationally disengaged, this corresponding to the resetting state, and a distal position in which the coupling member and outer drive member are rotationally engaged, this corresponding to the operational state. As will be described below, the fork member is actuated during user-operated cartridge change.

By providing a drive assembly with an "internal" coupling member as the axially actuated coupling component, it is possible to mount both the outer and inner drive members axially fixed as described above, this allowing e.g. the inner drive member in cooperation with the EOC member to serve as part of a safety system, this as described in WO 2007/017053.

The ring member 230 is mounted rotationally locked but axially free to the nut housing 240 and is biased distally by the compression spring 235, the ring thereby providing a distally directed force on an inserted cartridge. The functionality of the ring member as well as the distal housing 220 will be described together with components of the cartridge holder and housing assembly.

The cartridge holder and housing assembly 300 comprises a cap member 360, a user operated generally tubular actuation sleeve 310, a ring-formed sleeve mount 320, a cartridge holder 330, and an outer housing assembly comprising a tubular housing member 340, a magnifier lens 350, and a clip member 355 also serving as a lens mount. The cartridge holder is adapted to receive and hold a generally cylindrical drug-filled cartridge 390 provided with distal coupling means in the form of a needle hub mount 395 having, in the shown example, an external thread adapted to engage an inner thread of a corresponding hub of a needle assembly. In alternative embodiments the thread may be combined with or replaced by other connection means, e.g. a bayonet coupling. The hub mount further comprises a circumferential flange with a number of distally facing pointed projections 398 serving as a coupling means for the cartridge holder assembly as will be described in more detail below. A hub mount of the shown type is described in U.S. Pat. No. 5,693,027.

Functionally, in an assembled state, the cartridge holder 330 is mounted rotationally locked but axially free inside the actuation sleeve 310 which is mounted axially locked but rotationally moveable to the sleeve mount 320 which again is mounted axially and rotationally locked to the distal housing. The fork member 210 is mounted rotationally locked but axially free to the cartridge holder by means of the two fork legs 219 being received in opposed slots 339 formed in the cartridge holder. As will be described in detail below the combined sleeve mount and distal housing provide an inner circumferential control track in which pairs of opposed lateral control protrusions 333, 213 of respectively the cartridge holder and the fork member are received, the track providing controlled axial movement of respectively the cartridge holder and the fork member when the two components are rotated relative to the track by means of the user rotating the actuation sleeve. The sleeve mount is further provided with two pairs of stop surfaces 329 (see FIG. 5A) adapted to engage corresponding lateral stop surfaces provided on a pair of control extensions 319 arranged on the proximal end of the actuation sleeve, the stop surfaces providing rotational stops for the actuation sleeve.

The cartridge holder comprises a pair of opposed flexible arms 331 extending from a proximal ring portion, each arm being provided with a distal gripping portion, or "jaw", 335 having a plurality of proximal facing gripping teeth 338 spaced circumferentially to engage the above-described distally facing pointed projections 398 on the cartridge. A pair of longitudinally oriented opposed slots is formed between the arms, the slots each receiving a longitudinally oriented spline 314 formed on the inner surface of the actuation sleeve, this providing axially guided non-rotational engagement with the sleeve. Two opposed windows 332 are formed in the cartridge holder, one in each arm, each window being aligned with a corresponding window 312 formed in the outer tubular sleeve, the two pairs of windows moving together in rotational alignment. Corresponding to the embodiment of FIG. 2B each gripping portion 335 comprises an outer proximally-facing inclined and curved surface 337 adapted to engage a correspondingly curved distal circumferential edge 317 of the sleeve member 310, as well as a pair of inclined distally-facing edge portions 336 adapted to engage a pair of corresponding inclined proximally facing actuation surfaces 316 arranged on the inner surface of the actuation sleeve. By this arrangement the inclined actuation surfaces 336 will force the gripping shoulders outwardly to their open position as the actuation surfaces 336 are moved distally and into sliding contact with the sleeve actuation surfaces 316. Correspondingly, when the arms are moved proximally the outer curved surfaces 337 engage the actuation edges 317 and are thereby forced inwardly into their gripping position. As indicated above, axial movement of the cartridge holder is controlled by the cartridge holder control protrusions 333 being rotated in the control track by means of rotating the actuation sleeve.

As described above, the fork member is rotationally coupled to the cartridge holder via fork legs 219 and correspondingly rotates together therewith when the actuation sleeve is rotated, axial movement being controlled by the fork control protrusions 213 being received in the control track. To ensure that the piston rod is free to be pushed proximally during cartridge insertion, actuation of the cartridge holder between its receiving and gripping state and actuation of the drive coupling via the fork member take place in sequence. More specifically, in the shown embodiment full actuation of the cartridge holder takes place during a 60 degrees rotation of the actuation sleeve during which the fork member is not moved axially. When the cartridge thus has been properly locked in place and the piston rod correspondingly has been pushed to a corresponding proximal position, a subsequent 30 degrees further rotation of the actuation sleeve results in the drive coupling being actuated between the resetting state and the operational state by means of the fork member being moved distally during which the cartridge holder is not moved axially. In this way it is ensured to a high degree that the piston rod washer is positioned just in contact with the cartridge piston without build-up of tension in the system or creation of an air gap between the piston rod washer and the cartridge piston.

The ring member 230 comprises a ring portion, a pair of opposed radial guide protrusions 232 adapted to engage corresponding openings 242 in the nut housing, and a pair of opposed proximal protrusions 231. The latter each has a distal surface 233 adapted to engage the proximal edge of an inserted cartridge, as well as a proximal stop surface adapted to engage a corresponding distal stop surface on the fork member. For that purpose the fork member comprises a pair of circumferential arms 212 each providing a distal stop surface. As appears, the ring portion which encircles the cartridge holder merely serves as a carrier for the different protrusions. To prevent a user inserting a cartridge too deep into the cartridge holder, the ring member is actuated between a receiving and an operational state. More specifically, when the cartridge holder is in the initial receiving state with the gripping portions 335 fully apart, the user will insert the cartridge against the biasing force provided by the ring member. However, to prevent the cartridge from being pushed too deeply into the cartridge holder, the fork member provides via the above-described stop surfaces a proximal stop for the ring member, the stop position corresponding to a position somewhat distally of the fully inserted position. As the user then starts to rotate the actuation sleeve and the gripping portions are moved proximally the fork member stop surfaces 212 are rotated out of engagement with the ring member which is then allowed to be moved to its operational position as the cartridge is moved proximally by means of the gripping portions. In a front-loaded drug delivery device such an arrangement helps ensure that a cartridge is not inserted too deeply during initial loading of a cartridge, i.e. it can be prevented that the user pushes the piston rod too far proximally when the cartridge is inserted and thereby creates an air gap between the piston rod and the cartridge piston in the operational state in which the cartridge is mounted in the cartridge holder and the piston rod is locked in its operational state. As appears, depending on the actual design of the control track, the locking arms may start move proximally before the stop surfaces are rotated out of engagement with the ring member, however, to avoid tension in the system, the ring member should be free to move proximally when the gripping arms engage the cartridge and start pulling it proximally towards the biasing force from the ring member.

To prevent the user from releasing the expelling mechanism before the actuation sleeve has been fully rotated to its operational position, the fork member also serves to prevent a set and strained expelling mechanism from being released. More specifically, until the drive coupling is in the operational state the proximal-most surface of coupling member mounted on the fork element serves as a stop for the ratchet assembly thereby preventing the clutch member from being moved distally out of engagement with the housing and thus released. A further mechanism preventing a user from releasing the expelling mechanism before a cartridge has been mounted will be described below with reference to FIGS. 9A and 9B.

The outer housing 340 mainly serves to protect the interior components and to provide stiffness and an attractive outer appearance. Especially, the outer housing covers all the joints of the different inner housing parts.

Having described the individual components as well as the structural and functional relationship with reference to the exploded views of FIGS. 3 and 4, the functionality of certain subsystems will be described in greater detail with reference to FIGS. 5-9 illustrating the structural and functional interaction between individual components.

Figure 5A:
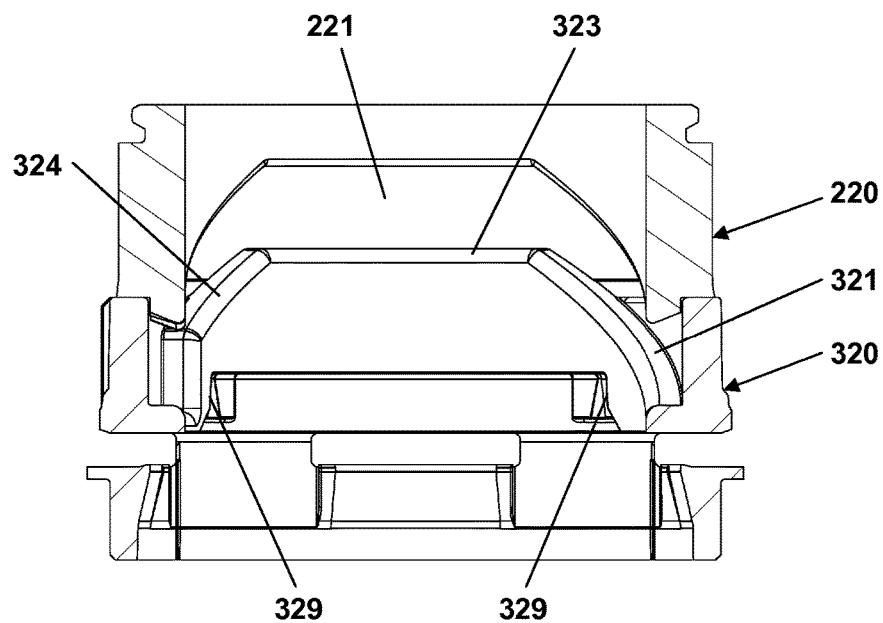
FIG. 5A shows in a sectional view a control track assembly.
Figure 5B:
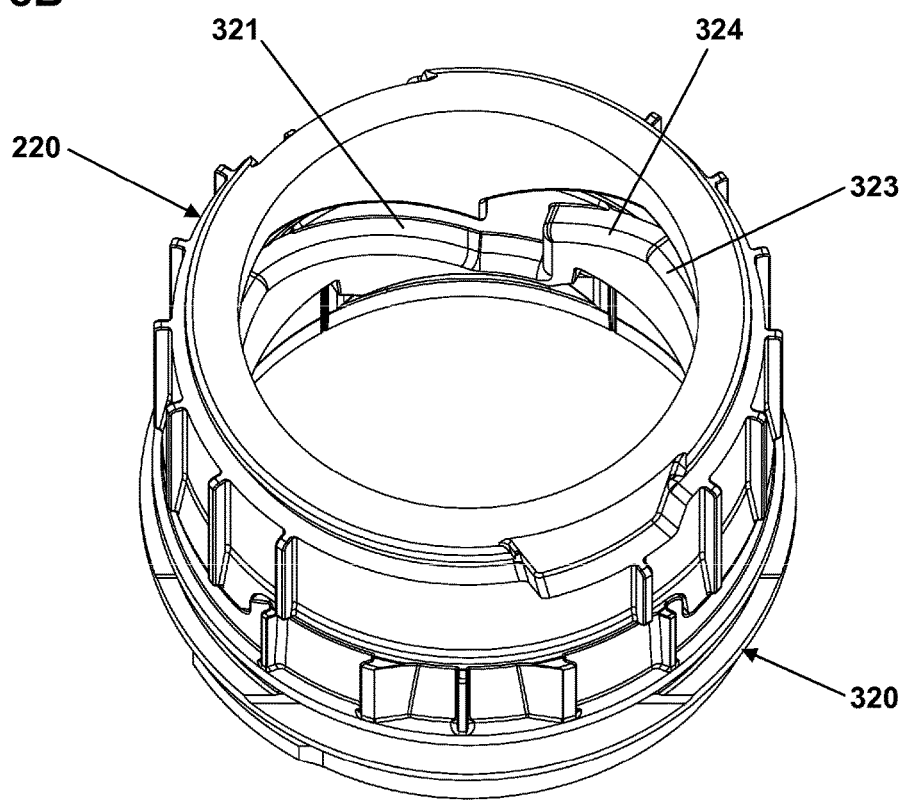
FIG. 5B shows in a perspective view the control track assembly.

More specifically, FIG. 5A shows in a sectional view a full 180 degrees half portion of the control track responsible for axial movement of one cartridge holder control protrusion and one fork member control protrusion, the opposed other half of the control track being into engagement with the other two control protrusions. The control track is formed by the sleeve mount 320 and the distal housing 220 in combination. FIG. 5B shows in a perspective view a portion of the control track. The shown track portions comprise (reference numerals refer to the sleeve part of the track) a cartridge holder slope portion 321 on the sleeve mount, an intermediate axially equidistant portion 323, and a fork member slope portion 324.

Figure 6A:
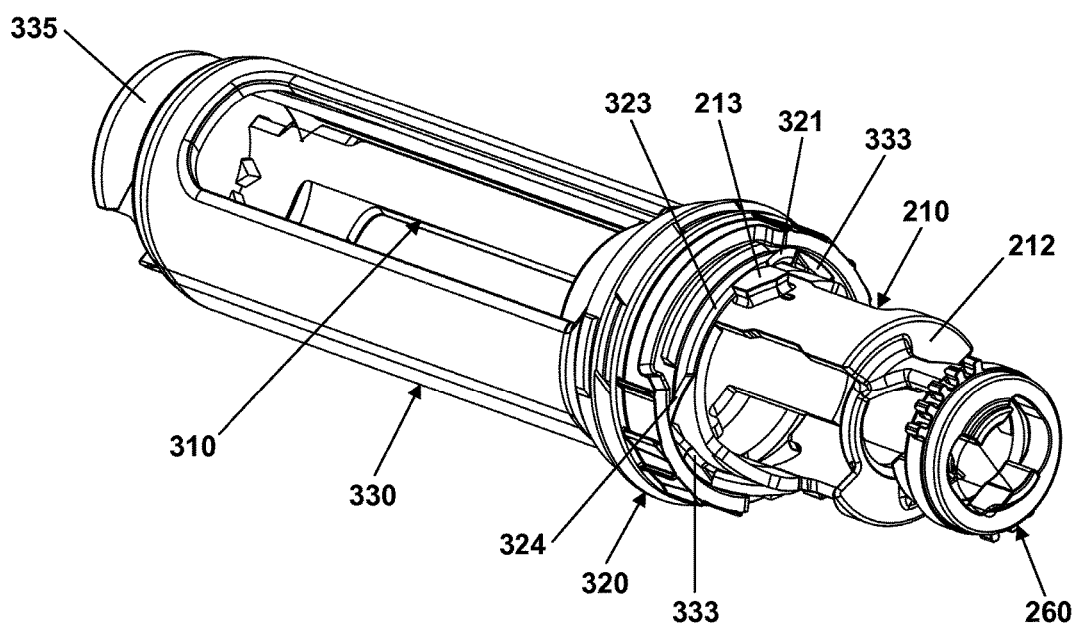
FIGS. 6A-6C show in perspective views a cartridge holder assembly in different operational states.
Figure 6B:
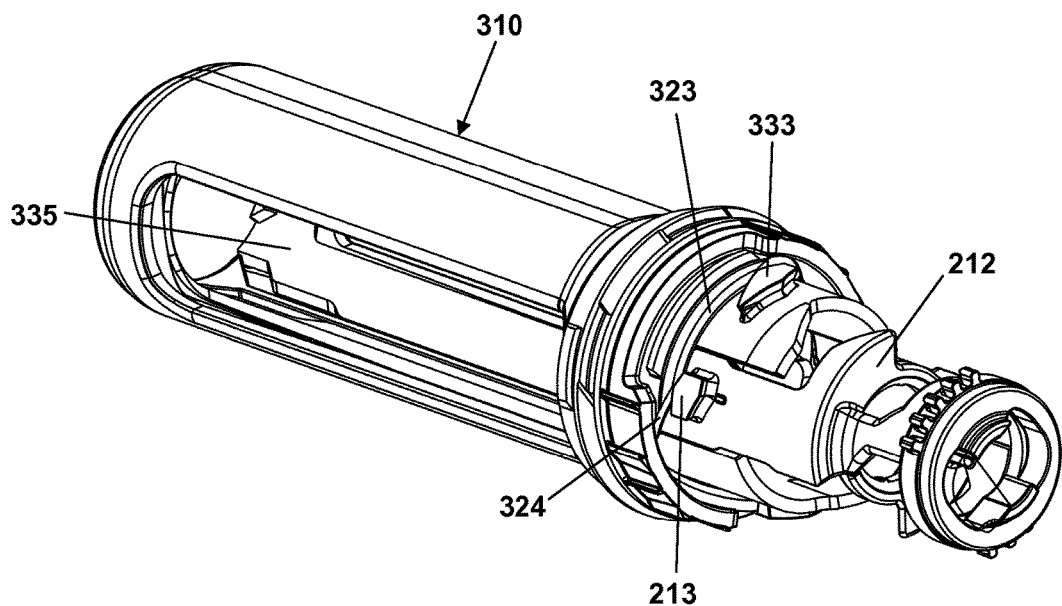
Figure 6C:
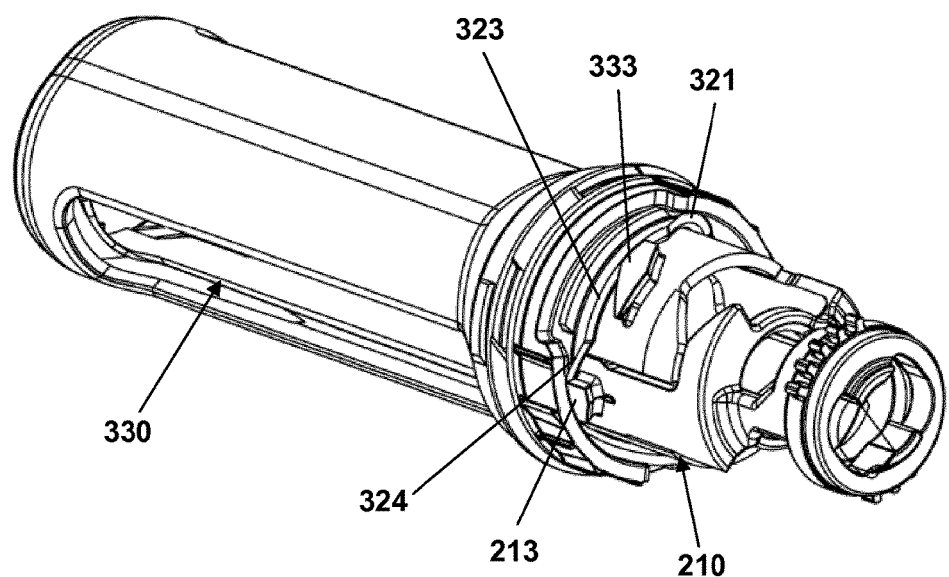

FIGS. 6A-6C illustrate in different operational states a cartridge holder assembly comprising the above-described cartridge holder 330, fork member 210, actuation sleeve 310, sleeve mount 320, and coupling member 260. As described above, the actuation sleeve is rotatable mounted in the sleeve mount which is mounted to the distal housing 220 to thereby form the control track, the cartridge holder is axially displaceable mounted in the actuation sleeve with the control protrusions 333 arranged in the control track, the fork member is axially displaceable mounted in the cartridge holder with the control protrusions 213 arranged in the control track, and the coupling member 260 is rotatable mounted on the fork member distal end. When the actuation sleeve is rotated the cartridge holder and therewith the fork member are rotated as well as moved axially via engagement with the control track. As the coupling member is rotationally locked to the inner drive member 270 it does not rotate relative to the piston rod, however, as the piston rod is pushed proximally during cartridge loading the piston rod and thereby the coupling member will rotate relative to the housing.

During cartridge loading for the shown embodiment the following operations take place. With the cartridge holder in its receiving state with the gripping portions 335 fully apart and in their distal-most position a used cartridge can be removed and a new cartridge can be inserted, this at the same time providing that the piston rod, which initially is positioned corresponding to the position of the piston in the used cartridge, is pushed proximally. As shown in FIG. 6A the cartridge holder control protrusions 333 are positioned in the distal end of the cartridge holder slope portions, and the fork member control protrusions 213 are positioned in the intermediate track portions just next to the cartridge holder slope portions.

Actuation of the cartridge holder then takes place during a 60 degrees rotation of the actuation sleeve during which the gripping portions are moved inwards and retracted to their proximal-most holding position. In this intermediate state the cartridge has been properly locked in place and the piston rod correspondingly has been pushed to a corresponding proximal position. The fork member is not moved axially during this operation but merely rotates. More specifically as shown in FIG. 6B, during the initial 60 degrees rotation of the actuation sleeve 310 the cartridge holder control protrusions 333 are moved proximally in the cartridge holder slope portions 321 and into the intermediate track portions 323 just next to the cartridge holder slope portions, and the fork member control protrusions 213 are moved in the intermediate track portions from just next to the cartridge holder slope portions to just next to the fork member slope portions 324.

Actuation of the drive coupling then takes place during a further 30 degrees rotation of the actuation sleeve during which the fork member is moved to its distal-most position with the coupling member in engagement with the outer drive member 250. The cartridge holder 330 is not moved axially during this operation but merely rotates. More specifically as shown in FIG. 6C, during the further 30 degrees rotation of the actuation sleeve the fork member 260 control protrusions 213 are moved distally in the fork member slope portions 324, and the cartridge holder control protrusions 333 are moved in the intermediate track portions 324 from just next to the cartridge holder slope portions 321 to the middle portion of the intermediate track portions 323. In this way it is ensured to a high degree that the piston rod washer is positioned just in contact with the cartridge piston without build-up of tension in the system.

When a loaded cartridge is to be replaced the above-described operations are performed in the reverse order by rotating the actuation sleeve a full 90 degrees in the opposite direction, whereby first the drive coupling disengages and then the cartridge holder is moved from its proximal holding position to its distal receiving position.

Although FIGS. 6A-6C for illustrative purposes do not show the ring member 230, it can be seen how the circumferential arms 212 of the fork member 260 is rotated during the initial cartridge holder actuation, thereby rotationally retracting the stop surfaces for the ring member, this allowing the biased ring member to be moved proximally by the cartridge.

With reference to FIGS. 6A-6C the combined actuation mechanism for the cartridge holder and the drive coupling was described. Next with reference to FIGS. 7A-7C the same operational states will be described focusing on the actual coupling elements per se.

Figure 7A:
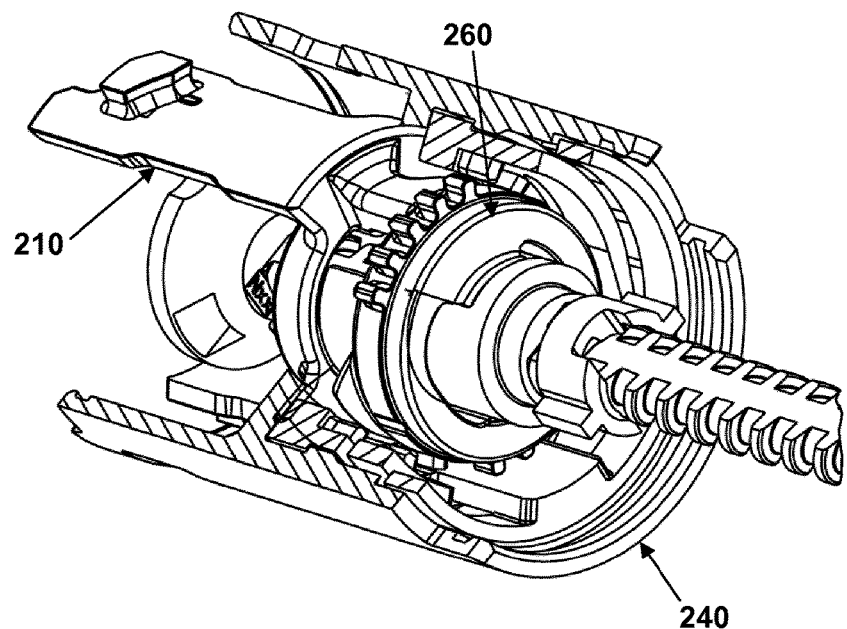
FIGS. 7A-7C show in perspective views a coupling assembly in operational states corresponding to FIGS. 6A-6C, FIG. 8 corresponds to FIG. 7A with some structures removed.
Figure 7B:
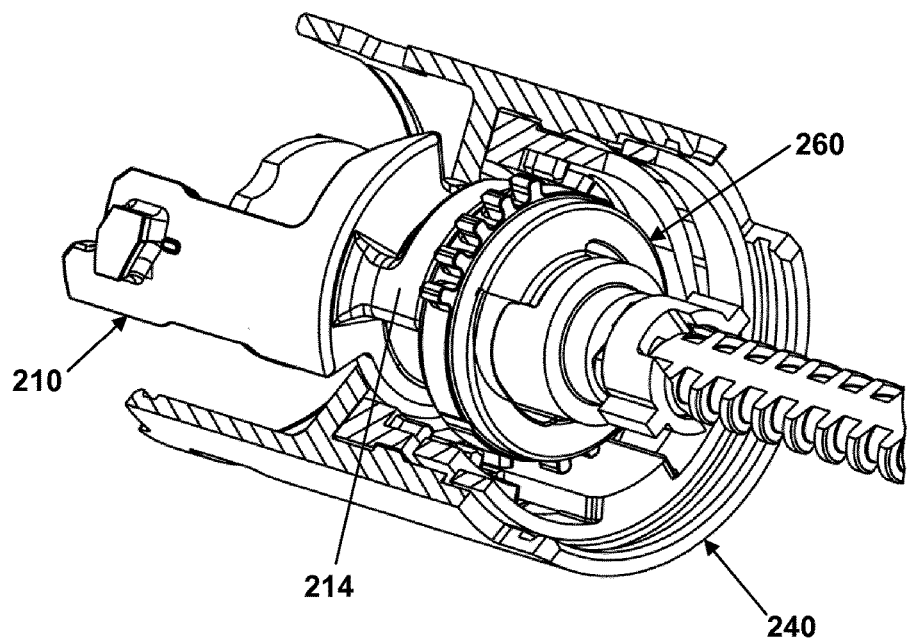
Figure 7C:
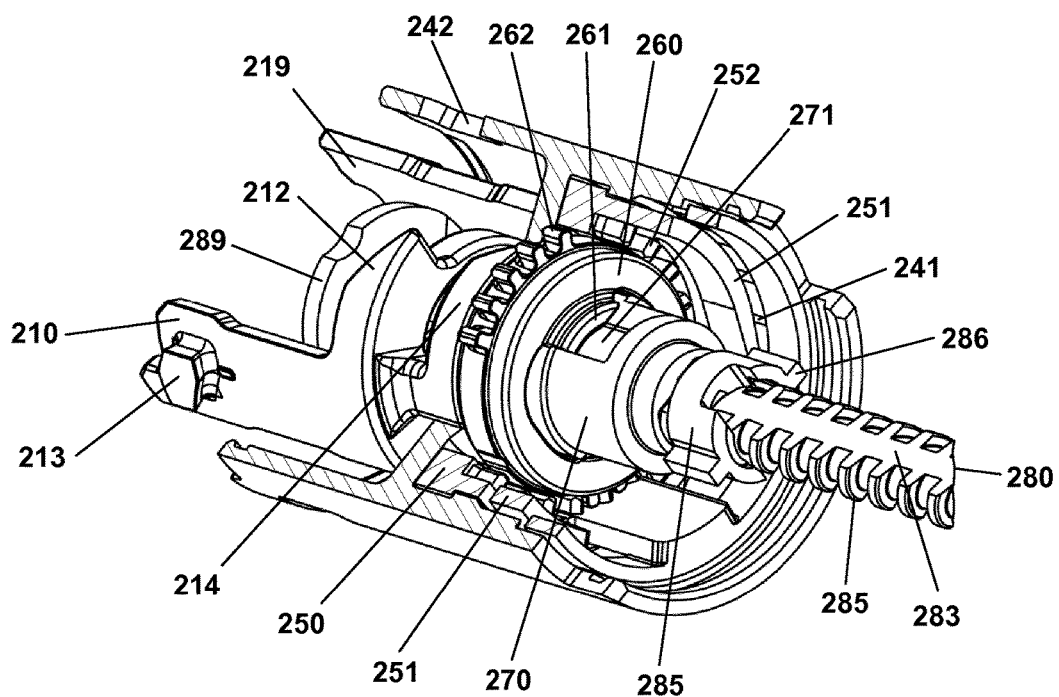

More specifically, FIG. 7C (providing the best view of the components) illustrates a coupling assembly comprising the above-described fork member 210, nut housing 240, the drive assembly comprising the outer drive member 250, the coupling member 260 and the inner drive member 270, the threaded piston rod 280, the EOC member 285 and the piston rod washer 289.

As described above, the inner drive member 270 is mounted axially locked but rotationally free on the central portion of the nut housing 240 by means of the circumferential flange 244 (see FIG. 8) surrounding the proximal opening of the nut bore and the pair of opposed gripping flanges 274 arranged on the distal end of the inner drive member. The piston rod is arranged through the two aligned bores with the threaded bore receiving the piston rod thread and with the two opposed planar surfaces 273 (see FIG. 4) of the inner drive member in engagement with the opposed planar surfaces 283 on the piston rod. On the piston rod the EOC member 285 and the washer 289 are mounted. The outer drive member 250 is mounted axially locked but rotationally free in the nut housing with the flexible ratchet arms 251 uni-directionally engaging the ratchet teeth 241 arranged on the nut housing inner surface.

The coupling member 260 is mounted axially locked but rotationally free on the proximal end portion 214 of the fork member 210, as well as rotationally locked but axially free on the inner drive member 270 via the cooperating spline structures 261, 271. The coupling member comprises circumferentially arranged outer coupling teeth 262 adapted to be moved axially in and out of engagement with the corresponding coupling teeth 252 arranged circumferentially on the inner surface of the outer drive member. By this arrangement the coupling member can be actuated via axial movement of the fork member (as described above with reference to FIGS. 6A-6C) from a proximal position in which the coupling member and outer drive member are rotationally disengaged (see FIG. 7A), this corresponding to the resetting state, via the intermediate state in which the fork member has been rotated but not moved axially (see FIG. 7B), to a distal position in which the coupling member and outer drive member are rotationally engaged, this corresponding to the operational state as shown in FIG. 7C.

Figure 8:
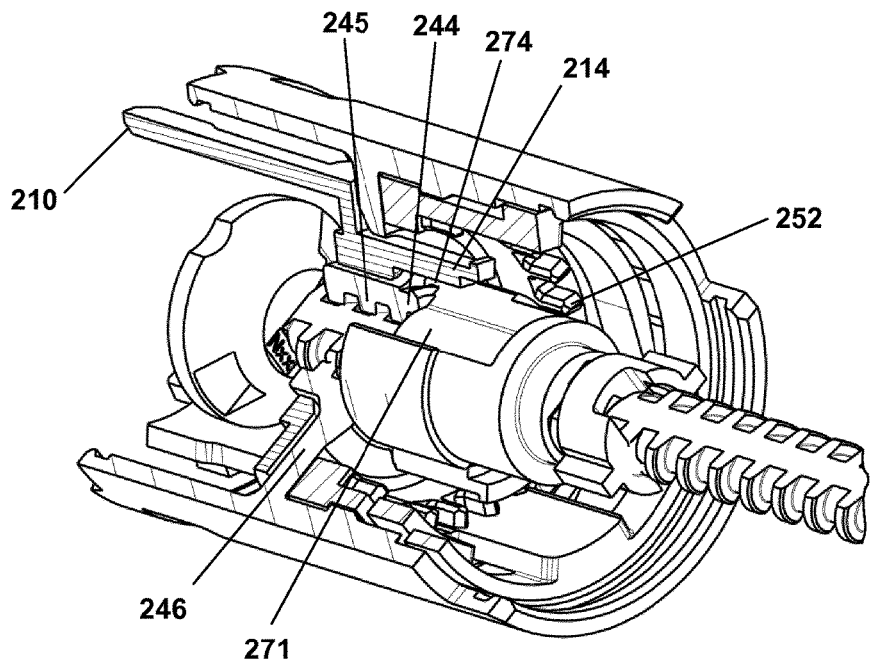

FIG. 8 corresponds to FIG. 7A, however, to better illustrate the mounting of the inner drive member 260 on the central nut portion via the above-described bearing structures 244, 274 the coupling member has been removed and the fork member 210 partially cut away.

Figure 9A:
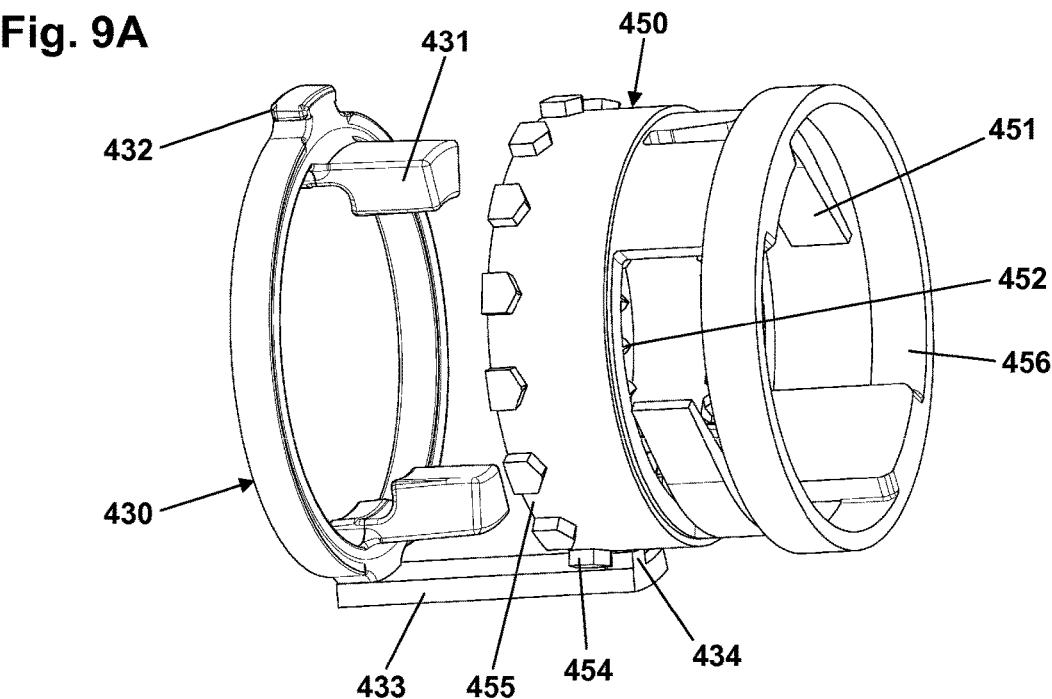
FIGS. 9A and 9B show in perspective views an alternative coupling assembly in different operational states.
Figure 9B:
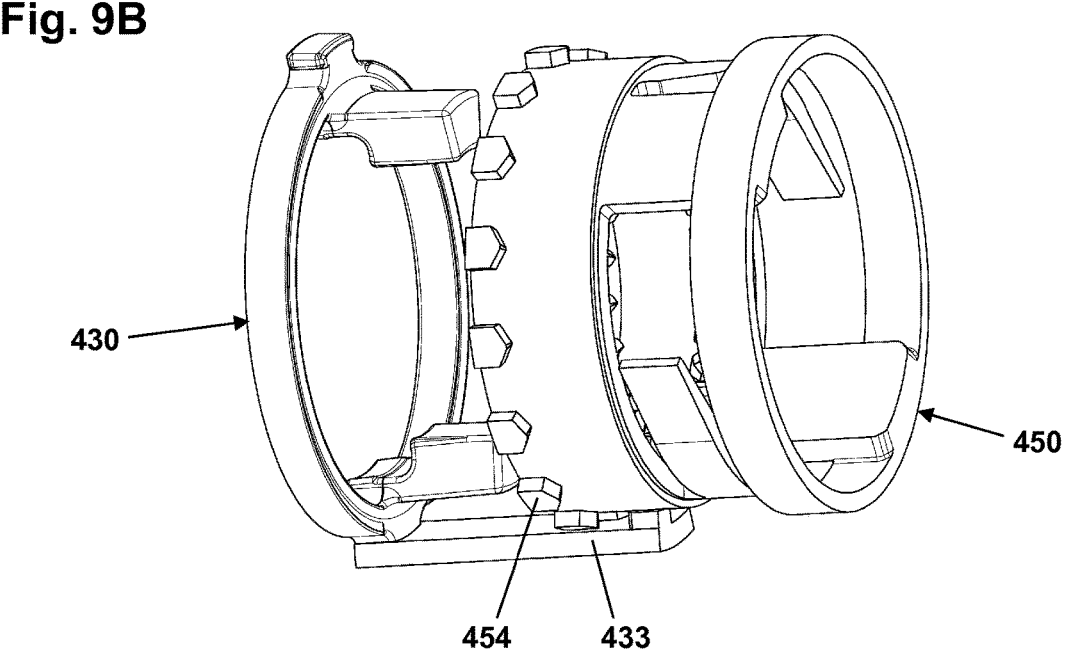

With reference to FIGS. 9A and 9B an alternative configuration of the ring member 230 and the outer drive member 250 of FIG. 4 will be described, the members having been modified to provide a lock against release of a set and strained expelling mechanism unless a cartridge has been loaded in the cartridge holder, irrespective of the state of the cartridge holding assembly.

More specifically, the ring member 430 comprises as the above-described ring member 230 a pair of opposed radial guide protrusions 432 adapted to engage openings in the nut housing, and a pair of opposed proximal protrusions 431. A control arm 433 extends proximally from one of the lateral guide protrusion as is provided with an inner control protrusion 434.

The control arm is guided in a corresponding longitudinal slot in a modified nut housing (not shown). The outer drive member 450 comprises as the above-described outer drive member 250 a pair of opposed ratchet arms 451, a plurality of coupling teeth 452 as well as a proximal supporting ring portion 456, however, in addition a plurality of teeth structures 454 are arranged circumferentially on the outer distal surface, the equidistantly arranged teeth providing a plurality of gaps 455 each configured to accommodate the control protrusion 434. When no cartridge is inserted in the cartridge holder the ring member and thereby also the control protrusion 434 is biased to its distal-most position by spring 235, whereby as shown in FIG. 9A the control protrusion is seated between two teeth structures 454 thereby preventing rotation of the outer drive member. When a cartridge has been loaded in the cartridge holder the ring member and thereby also the control protrusion 434 has been moved proximally and out of engagement with the outer drive member. When the cartridge is removed the spring 235 will return the ring member to its initial position and thereby move the control protrusion into blocking engagement with the outer drive member as shown in FIG. 9B. To facilitate seating of the control protrusion between the teeth both structures are provided with pointed surfaces on their facing ends.

As described above the scale drum 140 is in rotational threaded engagement with the inner surface of the inner proximal housing 201 via cooperating thread structures 142, 202. Whereas the proximal housing in the shown embodiment comprises a female thread in the form of an essentially complete helical groove 220, the scale drum is merely provided with a male thread in the form of a thread structure arranged corresponding to the proximal end portion of the scale drum. The scale drum thread structure could be in the form of a single flange structure spanning e.g. 360 degrees or be divided into a number of discrete flange portions or projections, i.e. "groove guides", engaging the helical groove. By arranging the scale drum outer thread structure at the end(s) only instead of circumferentially along the entire length of the drum it is possible to print the helically arranged rows of dose numerals closer to each other thereby allowing a shorter drum length for a given number of numerals.

Having described the different components of the expelling mechanism and their functional relationship as well as the operation of the cartridge holder and coupling, operation of the pen expelling mechanism will be described next with reference mainly to FIGS. 3 and 4.

The pen mechanism can be considered as two interacting systems, a dose system and a dial system. During dose setting the dial mechanism rotates and the torsion spring is loaded. The dose mechanism is locked to the housing and cannot move. When the push button is pushed down, the dose mechanism is released from the housing and due to the engagement to the dial system, the torsion spring will now rotate back the dial system to the starting point and rotate the dose system along with it.

The central part of the dose mechanism is the piston rod 280, the actual displacement of the piston being performed by the piston rod. During dose delivery, the piston rod is rotated by the inner drive member 270 and due to the threaded interaction with the threaded nut bore 245 which is fixed to the housing, the piston rod moves forward in the distal direction. Between the rubber piston and the piston rod, the piston washer 289 is placed which serves as a bearing for the rotating piston rod and evens out the pressure on the rubber piston. As the piston rod has a non-circular cross section where the piston rod drive member engages with the piston rod, the inner drive member is locked rotationally to the piston rod, but free to move along the piston rod axis. Consequently, rotation of the inner drive member results in a linear forwards (i.e. distal) movement of the piston. The outer drive member 250 is provided with small ratchet arms 251 which, via the coupling member 260, prevent the inner drive member from rotating clockwise (seen from the push button end). Due to the engagement with the inner drive member, the piston rod can thus only move forwards. During dose delivery, the inner drive member rotates anti-clockwise and the ratchet arms 251 provide the user with small clicks due to the engagement with the ratchet teeth on the nut housing inner surface, e.g. one click per unit of insulin expelled.

Turning to the dial system, the dose is set and reset by turning the dial member 170. When turning the dial member, the reset tube 130, the EOC member 285, the ratchet tube 120, the ratchet member 110 and the scale drum 140 all turn with it. As the ratchet tube is connected to the distal end of the torque spring 139 via the ratchet member, the spring is loaded. During dose setting, the arm 111 of the ratchet performs a dial click for each unit dialled due to the interaction with the inner teeth structure 291 of the clutch member 290. In the shown embodiment the clutch member is provided with 24 ratchet stops providing 24 clicks (increments) for a full 360 degrees rotation relative to the housing. The spring is preloaded during assembly which enables the mechanism to deliver both small and large doses within an acceptable speed interval. As the scale drum is rotationally engaged with the ratchet tube, but movable in the axial direction and the scale drum is in threaded engagement with the housing, the scale drum will move in a helical pattern when the dial system is turned, the number corresponding to the set dose being shown in the housing window 343.

The ratchet 110, 291 between the ratchet tube 120 and the clutch member 290 prevents the spring from turning back the parts. During resetting, the reset tube moves the ratchet arm 111, thereby releasing the ratchet click by click, one click corresponding to one unit IU of insulin in the described embodiment. More specifically, when the dial member is turned clockwise, the reset tube simply rotates the ratchet tube allowing the arm of the ratchet to freely interact with the teeth structures 291 in the clutch element. When the dial member is turned counter-clockwise, the reset tube interacts directly with the ratchet click arm forcing the click arm towards the centre of the pen away from the teeth in the clutch, thus allowing the click arm on the ratchet to move "one click" backwards due to torque caused by the loaded spring.

To deliver a set dose, the push button 180 is pushed in the distal direction by the user. The reset tube 130 decouples from the dial member as the toothed engagement 162, 172 between the dial member and the button module is moved axially apart (see below) and subsequently the clutch member 290 disengages the housing splines 204 and starts to rotate together with the outer drive member 270. Now the dial mechanism returns to "zero" together with the clutch member, the drive members 250, 270 and the coupling member 260, this leading to a dose of drug being expelled. It is possible to stop and start a dose at any time by releasing or pushing the push button at any time during drug delivery. A dose of less than 5 IU normally cannot be paused, since the rubber piston is compressed very quickly leading to a compression of the rubber piston and subsequently delivery of insulin when the piston returns to the original dimensions.

The EOC feature prevents the user from setting a larger dose than left in the cartridge. The EOC member 285 is rotationally locked to the reset tube, which makes the EOC member rotate during dose setting, resetting and dose delivery, during which it can be moved axially back and forth following the thread of the piston rod. When it reaches the proximal end of the piston rod a stop is provided, this preventing all the connected parts, including the dial member, from being rotated further in the dose setting direction by the spring, i.e. the now set dose corresponds to the remaining drug content in the cartridge.

The scale drum 140 is provided with a distal stop surface adapted to engage a corresponding stop surface on the housing inner surface, this providing a maximum dose stop for the scale drum preventing all the connected parts, including the dial member, from being rotated further in the dose setting direction. In the shown embodiment the maximum dose is set to 100 IU. Correspondingly, the scale drum is provided with a proximal stop surface adapted to engage a corresponding stop surface on the spring base member, this preventing all the connected parts, including the dial member, from being rotated further in the dose expelling direction, thereby providing a "zero" stop for the entire expelling mechanism. This said, the dial member may be provided with a torque limiter allowing it to be dialled past its normal stop position, see below.

To prevent accidental over-dosage in case something should fail in the dialling mechanism allowing the scale drum or the ratchet tube to move beyond their zero-position, the EOC member serves to provide a security system. More specifically, in an initial state with a full cartridge the EOC member is positioned in a distal-most axial position almost in contact with the inner drive element. After a given dose has been expelled the EOC member will again be positioned almost in contact with the inner drive element. Correspondingly, the EOC member will lock against the inner drive element in case the mechanism tries to deliver a dose beyond the zero-position. Due to tolerances and flexibility of the different parts of the mechanism the EOC will travel a short distance allowing a small "over dose" of drug to be expelled, e.g. 3-5 IU of insulin, however, as the inner drive element is axially fixed the tolerances and flexibility will normally be lower than in a system in which a drive element is axially moveable.

The expelling mechanism further comprises an end-of-dose (EOD) click feature providing a distinct feedback at the end of an expelled dose informing the user that the full amount of drug has been expelled. More specifically, the EOD function is made by the interaction between the spring base and the scale drum. When the scale drum returns to zero, a small click arm on the spring base is forced backwards by the progressing scale drum. Just before "zero" the arm is released and the arm hits a surface on the scale drum.

The shown mechanism is further provided with a torque limiter in order to protect the mechanism from overload applied by the user via the dial member. This feature is provided by the interface between the dial member 170 and the button module 160 which as described above are rotationally locked to each other during dose setting. More specifically, in the shown embodiment the dial member is provided with a circumferential inner teeth structure 172 engaging a number of corresponding teeth arranged on a flexible carrier portion 162 of the button module. The button module teeth are designed to transmit a torque of a given specified maximum size, e.g. 150-300 Nmm, above which the flexible carrier portion and the teeth will bend inwards and make the dial member turn without rotating the rest of the dial mechanism. Thus, the mechanism inside the pen cannot be stressed at a higher load than the torque limiter transmits through the teeth, this being the case for rotation in both directions.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device adapted to receive a cartridge comprising a cylindrical body portion, a distal outlet portion and an axially displaceable piston, the drug delivery device comprising:
   a housing,
   a front-loaded cartridge holder attached to the housing and adapted to receive and hold the cartridge, the front-loaded cartridge holder having:
   a receiving state in which the cartridge can be inserted and received in a proximal direction, and
   a holding state in which the inserted cartridge is held in an operational position, an expelling assembly comprising:
- a piston rod comprising an external thread and being adapted to engage and axially displace the piston in the loaded cartridge in a distal direction to thereby expel a dose of drug from the cartridge,
- a nut portion arranged non-moveable relative to the housing and comprising a threaded bore being in rotational engagement with the external thread of the piston rod,
- a primary drive element arranged in non-rotational engagement with the piston rod, the piston rod being axially moveable relatively to the primary drive element, whereby rotation of the primary drive element provides that the piston rod is moved axially through the nut portion,
- a drive assembly adapted to rotate the primary drive element,
- a drive coupling being actuatable between:
  - a resetting state in which the piston rod can be moved proximally, and
  - an operational state in which the primary drive element can drive the piston rod distally,
- a user operated actuation structure actuatable from a loading state to an operational state, wherein:
- the cartridge holder is actuated from the receiving state to the holding state when the user operated actuation structure is actuated from the loading state to the operational state, and
- the drive coupling is actuated from the resetting state to the operational state when the user operated actuation structure is actuated from the loading state to the operational state,
- wherein the primary drive element is not moved axially relative to the housing when the drive coupling is actuated wherein the user operated actuation structure is actuatable from the loading state through an intermediate state to the operational state, wherein:
- the cartridge holder is actuated from the receiving state to the holding state when the user operated actuation structure is actuated from the loading state to the intermediate state, and
- the drive coupling is actuated from the resetting state to the operational state when the user operated actuation structure is actuated from the intermediate state to the operational state.

2. The drug delivery device as in claim 1, wherein the primary drive element is connected axially locked to the nut portion.

3. The drug delivery device as in claim 1, further comprising a secondary drive element rotationally driven by the drive assembly, the drive coupling comprising a coupling element moveable by the user operated actuation structure between:
- a resetting position, corresponding to the resetting state, wherein the primary and secondary drive elements are rotationally de-coupled, and
- an operational position corresponding to the operational state, wherein the primary and secondary drive elements are rotationally coupled.

4. The drug delivery device as in claim 3, wherein the secondary drive element is axially locked relative to the housing, the coupling element being axially moveable between the resetting and operational positions.

5. The drug delivery device as in claim 3, wherein the primary drive element, the drive coupling and the secondary drive element are arranged concentrically.

6. The drug delivery device as in claim 1, wherein the front-loaded cartridge holder is adapted to be connected to the housing by a relative motion there between, the front-loaded cartridge holder serving as the actuation structure.

7. The drug delivery device as in claim 1, wherein the drive assembly further comprises a setting structure allowing a user to set a dose amount to be expelled.

8. The drug delivery device as in claim 7, wherein the drive assembly further comprises:
- a stop member in threaded engagement with the piston rod,
- a setting member coupled to the setting structure such that rotation of the setting structure during dose setting causes the setting member to rotate,
- wherein the stop member is coupled to the setting member and the piston rod such that relative rotation between the setting member and the piston rod during dose setting causes the stop member to move proximally on the piston rod, and
- wherein the stop member rotates with the piston rod during dose expelling, the stop member abutting a proximally-facing surface of the primary drive element when the set dose has been expelled.

9. The drug delivery device as in claim 7, wherein the drive assembly further comprises:
- a drive spring being strained during dose setting corresponding to the set dose, and
- a user actuated release structure for releasing the drive spring to thereby move the piston rod in the distal direction corresponding to the set dose.

* * * * *